US008524461B2

(12) United States Patent
Kalish et al.

(10) Patent No.: US 8,524,461 B2
(45) Date of Patent: Sep. 3, 2013

(54) MULTIPLE ANTIGENIC PEPTIDE ASSAY FOR DETECTION OF HIV OR SIV TYPE RETROVIRUSES

(75) Inventors: Marcia L. Kalish, Decatur, GA (US); Clement B. Ndongmo, Decatur, GA (US); Chou-Pong Pau, Decatur, GA (US); William M. Switzer, Stone Mountain, GA (US); Thomas M. Folks, Lithonia, GA (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 473 days.

(21) Appl. No.: 12/717,276

(22) Filed: Mar. 4, 2010

(65) Prior Publication Data

US 2010/0222236 A1 Sep. 2, 2010

Related U.S. Application Data

(63) Continuation of application No. 10/552,182, filed as application No. PCT/US2004/011022 on Apr. 8, 2004, now abandoned.

(60) Provisional application No. 60/462,071, filed on Apr. 11, 2003.

(51) Int. Cl.
*G01N 33/53* (2006.01)
*A61K 39/21* (2006.01)

(52) U.S. Cl.
USPC .............................. 435/7.2; 435/5; 424/202.1

(58) Field of Classification Search
None
See application file for complete search history.

(56) References Cited

U.S. PATENT DOCUMENTS

| | | | |
|---|---|---|---|
| 5,580,563 | A | 12/1996 | Tam |
| 5,622,933 | A | 4/1997 | Sabatier |
| 5,800,983 | A | 9/1998 | Bridon et al. |
| 6,149,910 | A | 11/2000 | DeLeys et al. |
| 6,150,088 | A | 11/2000 | Chan et al. |
| 6,210,903 | B1 | 4/2001 | DeLeys |
| 6,372,426 | B1 | 4/2002 | Zens |
| 6,379,679 | B1 | 4/2002 | Mabrouk et al. |

(Continued)

FOREIGN PATENT DOCUMENTS

| | | |
|---|---|---|
| AU | 0737857 B2 | 8/2001 |
| WO | WO 93/03766 | 3/1993 |
| WO | WO 95/33206 | 12/1995 |
| WO | WO 98/26075 | 6/1998 |

OTHER PUBLICATIONS

Ayouba et al., "HIV-1 group N among HIV-1 seropositive individuals in Cameroon," *AIDS* 14(16):2623-2325, 2000.

(Continued)

*Primary Examiner* — Bao Li
(74) *Attorney, Agent, or Firm* — Klarquist Sparkman, LLP

(57) ABSTRACT

A method for detecting at least one antibody directed against at least one primate immunodeficiency virus in a biological sample that includes contacting a biological sample with (i) at least one detection multiple antigenic peptide comprising a portion of an immunodominant region of a transmembrane protein of a primate immunodeficiency virus and (ii) at least one differentiation multiple antigenic peptide comprising a portion of a V3-loop of an envelope protein of a primate immunodeficiency virus. Also disclosed is an enzyme immunoassay that includes a first substrate to which are bound at least one of the detection multiple antigenic peptides and a second substrate to which are bound at least one of the differentiation multiple antigenic peptides.

25 Claims, 3 Drawing Sheets

(56) References Cited

U.S. PATENT DOCUMENTS

| | | | |
|---|---|---|---|
| 6,399,067 | B1 | 6/2002 | Goldstein |
| 6,509,018 | B1 | 1/2003 | Mauclere et al. |
| 2002/0052469 | A1 | 5/2002 | Fujii et al. |

OTHER PUBLICATIONS

Campbell et al., "Extensive ENV gene heterogeneity in tissues from SIV infected macaques," *Symp Nonhum Primate Models AIDS* Abstract No. 31, 1993.

Chiodi et al., "Site-Directed ELISA With Synthetic Peptides Representing the HIV transmembrane Glycoprotein," *Journal of Medical Virology* 23:1-9, 1987.

Courgnaud et al., "Partial Molecular Characterization of Two Simian Immunodeficiency Viruses (SIV) from Africa Colobids: SIVwrc from Western Red Colobus (*Piliocolobus badius*) and SIVolc from Olive Colobus (*Procolobus verus*),"Journal of Virology 77(1):744-748, 2003.

Courgnaud et al., "Identification of a New Simian Immunodeficiency Virus Lineage with a *vpu* Gene Present among Different *Cercopithecus* Monkeys (*C. mona, C. cephus*, and *C. nictitans*) from Cameroon," Journal of Virology 77(23):12523-12534, 2003.

Fenouillet et al., "Early and specific diagnosis of seropositivity of HIVs by an anzyme-linked immunosorbent assay using env-derived synthetic peptides," *Aids* 4:1137-1140, 1990.

Gnann, Jr. et al., "Fine Mapping of an immunodominant Domain in the Transmembrane Glycoprotein of Human Immunodeficiency Virus," *Journal of Virology* 61(8):2639-2641, 1987.

Hahn et al., "AIDS as a Zoonosis: Scientific and Public Health Implications," *Science* 287:607-614, 2000.

Hirsch et al., "Characterization of a Novel Simian Immunodeficiency Virus (SIV) from L'Hoest Monkeys (*Cercopithecus l'hoesti*): Implications for the Origins of SIVmnd and Other Primate Lentiviruses," *Journal of Virology*, 72(2):1036-1045, 1999.

Jackwood and Hilt, "Production and immunogenicity of multiple antigenic peptide (MAP) constructs derived from the S1 glycoprotein of infectious bronchitis virus (IBV)," *Adv. Exp. Med. Biol*., 380:213-219, 1995, Abstract Only.

Kent et al., "B-cell Epitopes on the Envelope Glycoproteins of SIV and HIV-2," pp. IV-5 to IV-21, 1996.

Kim et al., "Comparing tandem repeats and multiple antigenic peptides as the antigens to detect antibodies by enzyme immunoassay," *J. Immunol. Meth*. 257:51-54, 2001.

Masciotra et al., "Serological Detection of Infection with Diverse Human and Simian Immunodeficiency Viruses Using Consensus *env* Peptides," *Clinical and Diagnostic Laboratory Immunology* 7(4):706-709, 2000.

Miller et al., "Identification of Broadly Reactive Continuous Antigenic Determinants of Simian Immunodeficiency Virus Glycoproteins," *AIDS Research and Human Retroviruses*, 8(6):1153-1164, 1992.

Ndongmo et al., "New multiple antigenic peptide-based enzyme immunoassay for detection of simian immunodeficiency virus infection in nonhuman primates and humans," *J. Clin. Microbiol.* 42(11):5161-5169, 2004.

Pau et al., "Antigenic Variation and Serotyping of HIV Type 1 from Four World Health Organization-Sponsored HIV Vaccine Sites," *Aids Research and Human Retroviruses* 10(11):1369-1377, 1994.

Peeters et al., "Risk to Human Health from a Plethora of Simian Immunodeficiency Viruses in Primate Bushmeat," *CDC* 8(5):1-12, 2002.

Reeves et al., "Human immunodeficiency virus type 2," *Journal of General Virology* 83:1253-1265, 2002.

Ribiero-Rodrigues et al., "Performance characteristics of a rapid new immunochromatographic test for detection of antibodies to human immunodeficiency virus," *Clin. Diagn. Lab. Immunol.* 10(2):303-307, 2003.

Santiago et al., "Amplification of a Complete Simian Immunodeficiency Virus Genome from Fecal RNA of a Wild Chimpanzee," *Journal of Virology* 77(3):2233-2242, 2003.

Shin et al., "Use of Multiple Antigenic Peptides as Coating Antigens in Detection of Antibody," *Mol. Cells*. 6(2):169-175, 1996.

Shin et al., "The Use of Multiple Antigenic Peptide (MAP) in the Immunodiagnosis of Human Immunodeficiency Virus Infection," *Biochemistry and Molecular Biology International* 43(4):713-721, 1997.

Simon et al., "Synthetic peptide strategy for the detection of and discrimination among highly divergent primate lentiviruses," *Aids Res. Hum. Retroviruses*, 17(10):937-952, 2001.

Silvera et al., "Fine Analysis of Humoral Antibody Response to Envelope Glycoprotein of SIV in Infected and Vaccinated Macaques," *Aids Res. Hum. Retroviruses*, 10(10):1295-1304, 1994.

Tam, "Multiple antigen peptide," *Journal of Immunological Methods*, 124:53-61, 1989.

Tam, "Synthetic peptide vaccine design: Synthesis and properties of a high-density multiple antigenic peptide system," *Proc. Natl. Acad. Sci. USA* 85:5409-5413, 1988.

Tang et al., "Minimum Requirements for Immunogenic and Antigenic Activities of Homologs of a Synthetic Peptide of Influenza Virus Hemagglutinin," *J. Virol*., 62(12):4745-4751, 1988.

Tsujimoto et al., "Isolation and Characterization of Simian Immunodeficiency Virus from Mandrills in Africa and Its Relationship to Other Human and Simian Immunodeficiency Viruses," *J. Virol*., 62(11):4044-4050, 1988.

Zvelebil et al., "Predictions of linear T-cell and B-cell epitopes in proteins encoded by HIV-1, HIV-2 and SIVmac and the conservation of these sites between strains," *Febs Lett*. 242(1):9-21, 1988.

International Search Report, International Publication No. WO 2004/092724 A3, published Oct. 28, 2004.

```
                         SEQUENCE LISTING


<160> NUMBER OF SEQ ID NOS: 31

<210> SEQ ID NO 1
<211> LENGTH: 11
<212> TYPE: PRT
<213> ORGANISM: Artificial Sequence
<220> FEATURE:
<223> OTHER INFORMATION: SIVcpzGab virus

<400> SEQUENCE: 1

Trp Gly Cys Ser Gly Lys Ala Val Cys Tyr Thr
1               5                   10


<210> SEQ ID NO 2
<211> LENGTH: 11
<212> TYPE: PRT
<213> ORGANISM: Artificial Sequence
<220> FEATURE:
<223> OTHER INFORMATION: SIVcpzCam virus

<400> SEQUENCE: 2

Trp Gly Cys Ser Gly Lys Ala Ile Cys Tyr Thr
1               5                   10


<210> SEQ ID NO 3
<211> LENGTH: 11
<212> TYPE: PRT
<213> ORGANISM: Artificial Sequence
<220> FEATURE:
<223> OTHER INFORMATION: SIVcpzAnt virus

<400> SEQUENCE: 3

Trp Gly Cys Ala Asp Lys Val Ile Cys His Thr
1               5                   10


<210> SEQ ID NO 4
<211> LENGTH: 11
<212> TYPE: PRT
<213> ORGANISM: Artificial Sequence
<220> FEATURE:
```

<223> OTHER INFORMATION: SIVsm virus

<400> SEQUENCE: 4

Trp Gly Cys Ala Phe Arg Gln Val Cys His Thr
1 5 10

<210> SEQ ID NO 5
<211> LENGTH: 11
<212> TYPE: PRT
<213> ORGANISM: Artificial Sequence
<220> FEATURE:
<223> OTHER INFORMATION: SIVagm-1 virus

<400> SEQUENCE: 5

Trp Gly Cys Ala Trp Lys Gln Val Cys His Thr
1 5 10

<210> SEQ ID NO 6
<211> LENGTH: 11
<212> TYPE: PRT
<213> ORGANISM: Artificial Sequence
<220> FEATURE:
<223> OTHER INFORMATION: SIVagm-2 virus

<400> SEQUENCE: 6

Trp Gly Cys Ala Phe Lys Gln Val Cys His Thr
1 5 10

<210> SEQ ID NO 7
<211> LENGTH: 11
<212> TYPE: PRT
<213> ORGANISM: Artificial Sequence
<220> FEATURE:
<223> OTHER INFORMATION: SIVsun/lhoest virus

<400> SEQUENCE: 7

Trp Gly Cys Gln Trp Lys Gln Val Cys His Thr
1 5 10

<210> SEQ ID NO 8
<211> LENGTH: 11
<212> TYPE: PRT
<213> ORGANISM: Artificial Sequence
<220> FEATURE:
<223> OTHER INFORMATION: SIVcol virus

<400> SEQUENCE: 8

Ile Gly Cys Ala Asn Met Gln Ile Cys Arg Thr
1 5 10

<210> SEQ ID NO 9
<211> LENGTH: 11
<212> TYPE: PRT
<213> ORGANISM: Artificial Sequence
<220> FEATURE:
<223> OTHER INFORMATION: SIVrcm virus

<400> SEQUENCE: 9

Phe Gly Cys Ala Trp Arg Gln Val Cys His Thr
1 5 10

<210> SEQ ID NO 10
<211> LENGTH: 11
<212> TYPE: PRT
<213> ORGANISM: Artificial Sequence
<220> FEATURE:
<223> OTHER INFORMATION: SIVmnd14 virus

<400> SEQUENCE: 10

Trp Gly Cys Ser Phe Ser Gln Val Cys His Thr
1 5 10

<210> SEQ ID NO 11
<211> LENGTH: 11
<212> TYPE: PRT
<213> ORGANISM: Artificial Sequence
<220> FEATURE:
<223> OTHER INFORMATION: SIVmndGB1 virus

<400> SEQUENCE: 11

Trp Gly Cys Ser Trp Ala Gln Val Cys His Thr
1 5 10

<210> SEQ ID NO 12
<211> LENGTH: 11
<212> TYPE: PRT
<213> ORGANISM: Artificial Sequence
<220> FEATURE:
<223> OTHER INFORMATION: SIVsyk virus

<400> SEQUENCE: 12

Trp Gly Cys Ala Phe Lys Gln Ile Cys His Thr
1 5 10

<210> SEQ ID NO 13
<211> LENGTH: 11
<212> TYPE: PRT
<213> ORGANISM: Artificial Sequence
<220> FEATURE:
<223> OTHER INFORMATION: SIVdeb virus

<400> SEQUENCE: 13

Trp Gly Cys Ala Phe Lys Gln Ile Cys His Thr
1 5 10

<210> SEQ ID NO 14
<211> LENGTH: 15
<212> TYPE: PRT
<213> ORGANISM: Artificial Sequence
<220> FEATURE:
<223> OTHER INFORMATION: SIVcpzGab virus

<400> SEQUENCE: 14

Arg Gly Glu Val Gln Ile Gly Pro Gly Met Thr Phe Tyr Asn Ile
1 5 10 15

<210> SEQ ID NO 15
<211> LENGTH: 15
<212> TYPE: PRT
<213> ORGANISM: Artificial Sequence
<220> FEATURE:
<223> OTHER INFORMATION: SIVsm virus

<400> SEQUENCE: 15

Val Leu Pro Val Thr Ile Met Ser Gly Leu Val Phe His Ser Gln
1 5 10 15

<210> SEQ ID NO 16
<211> LENGTH: 15
<212> TYPE: PRT
<213> ORGANISM: Artificial Sequence
<220> FEATURE:
<223> OTHER INFORMATION: SIVagm virus

<400> SEQUENCE: 16

Val Leu Pro Val Thr Ile Met Ala Gly Leu Val Phe His Ser Gln
1 5 10 15

<210> SEQ ID NO 17
<211> LENGTH: 15
<212> TYPE: PRT
<213> ORGANISM: Artificial Sequence
<220> FEATURE:
<223> OTHER INFORMATION: SIVsyk virus

<400> SEQUENCE: 17

Ile Lys Asn Ile Gln Leu Ala Ala Gly Tyr Phe Leu Pro Val Ile
1 5 10 15

<210> SEQ ID NO 18
<211> LENGTH: 15
<212> TYPE: PRT
<213> ORGANISM: Artificial Sequence
<220> FEATURE:
<223> OTHER INFORMATION: SIV1hoest virus

<400> SEQUENCE: 18

Glu Val Ser Thr Ile Ser Ser Thr Gly Leu Leu Phe Tyr Tyr Gly
1 5 10 15

<210> SEQ ID NO 19
<211> LENGTH: 15
<212> TYPE: PRT
<213> ORGANISM: Artificial Sequence
<220> FEATURE:
<223> OTHER INFORMATION: SIVcol virus

<400> SEQUENCE: 19

His Arg Asn Leu Asn Thr Ala Asn Gly Ala Lys Phe Tyr Tyr Glu
1 5 10 15

<210> SEQ ID NO 20
<211> LENGTH: 15
<212> TYPE: PRT
<213> ORGANISM: Artificial Sequence
<220> FEATURE:
<223> OTHER INFORMATION: SIVrcm virus

<400> SEQUENCE: 20

Val Lys Gly Ile Ser Leu Ala Thr Gly Val Phe Ile Ser Leu Arg
1 5 10 15

<210> SEQ ID NO 21
<211> LENGTH: 15
<212> TYPE: PRT
<213> ORGANISM: Artificial Sequence
<220> FEATURE:
<223> OTHER INFORMATION: SIVmnd14 virus

<400> SEQUENCE: 21

Ile Val Ser Val Pro Ser Ala Ser Gly Leu Ile Phe Tyr His Gly
1 5 10 15

<210> SEQ ID NO 22
<211> LENGTH: 15
<212> TYPE: PRT
<213> ORGANISM: Artificial Sequence
<220> FEATURE:
<223> OTHER INFORMATION: SIVdeb virus

<400> SEQUENCE: 22

Tyr Arg Ala Val His Met Ala Thr Gly Leu Ser Phe Tyr Thr Thr
1 5 10 15

<210> SEQ ID NO 23
<211> LENGTH: 28
<212> TYPE: PRT
<213> ORGANISM: Artificial Sequence
<220> FEATURE:
<223> OTHER INFORMATION: SIVcpzGab virus

<400> SEQUENCE: 23

```
Asn Asn Thr Arg Gly Glu Val Gln Ile Gly Pro Gly Met Thr Phe Tyr
1               5                   10                  15

Asn Ile Glu Asn Val Val Gly Asp Thr Arg Ser Ala
            20                  25
```

<210> SEQ ID NO 24
<211> LENGTH: 28
<212> TYPE: PRT
<213> ORGANISM: Artificial Sequence
<220> FEATURE:
<223> OTHER INFORMATION: SIVmnd virus

<400> SEQUENCE: 24

```
Asn Arg Ser Val Val Ser Thr Pro Ser Ala Thr Gly Leu Leu Phe Tyr
1               5                   10                  15

His Gly Leu Glu Pro Gly Lys Asn Leu Lys Lys Gly
            20                  25
```

<210> SEQ ID NO 25
<211> LENGTH: 28
<212> TYPE: PRT
<213> ORGANISM: Artificial Sequence
<220> FEATURE:
<223> OTHER INFORMATION: SIVagm virus

<400> SEQUENCE: 25

```
Asn Lys Thr Val Leu Pro Val Thr Ile Met Ala Gly Leu Val Phe His
1               5                   10                  15

Ser Gln Lys Tyr Asn Thr Arg Leu Arg Arg Gln Ala
            20                  25
```

<210> SEQ ID NO 26
<211> LENGTH: 27
<212> TYPE: PRT
<213> ORGANISM: Artificial Sequence
<220> FEATURE:
<223> OTHER INFORMATION: SIVsm virus

<400> SEQUENCE: 26

```
Asn Lys Thr Val Leu Pro Val Thr Ile Met Ser Gly Leu Val Phe His
1               5                   10                  15

Ser Gln Pro Ile Asn Glu Arg Pro Lys Gln Ala
            20                  25
```

<210> SEQ ID NO 27
<211> LENGTH: 24
<212> TYPE: PRT
<213> ORGANISM: Artificial Sequence
<220> FEATURE:
<223> OTHER INFORMATION: SIVcpzGab virus

<400> SEQUENCE: 27

```
Leu Ala Val Glu Arg Tyr Leu Gln Asp Gln Gln Ile Leu Gly Leu Trp
1               5                   10                  15

Gly Cys Ser Gly Lys Ala Val Cys
            20
```

```
<210> SEQ ID NO 28
<211> LENGTH: 24
<212> TYPE: PRT
<213> ORGANISM: Artificial Sequence
<220> FEATURE:
<223> OTHER INFORMATION: SIVmnd virus

<400> SEQUENCE: 28

Thr Ser Leu Glu Asn Tyr Ile Lys Asp Gln Ala Leu Leu Ser Gln Trp
1               5                   10                  15

Gly Cys Ser Trp Ala Gln Val Cys
            20


<210> SEQ ID NO 29
<211> LENGTH: 24
<212> TYPE: PRT
<213> ORGANISM: Artificial Sequence
<220> FEATURE:
<223> OTHER INFORMATION: SIVagm virus

<400> SEQUENCE: 29

Thr Ala Leu Glu Lys Tyr Leu Glu Asp Gln Ala Arg Leu Asn Ile Trp
1               5                   10                  15

Gly Cys Ala Phe Arg Gln Val Cys
            20


<210> SEQ ID NO 30
<211> LENGTH: 24
<212> TYPE: PRT
<213> ORGANISM: Artificial Sequence
<220> FEATURE:
<223> OTHER INFORMATION: SIVsm virus

<400> SEQUENCE: 30

Thr Ala Ile Glu Lys Tyr Leu Lys Asp Gln Ala Lys Leu Asn Ser Trp
1               5                   10                  15

Gly Cys Ala Phe Arg Gln Val Cys
            20


<210> SEQ ID NO 31
<211> LENGTH: 11
<212> TYPE: PRT
<213> ORGANISM: Artificial Sequence
<220> FEATURE:
<223> OTHER INFORMATION: synthetic IDR MAP construct
<220> FEATURE:
<221> NAME/KEY: misc_feature
<222> LOCATION: (1)..(1)
<223> OTHER INFORMATION: Xaa can be W, I, or F
<220> FEATURE:
<221> NAME/KEY: misc_feature
<222> LOCATION: (4)..(4)
<223> OTHER INFORMATION: Xaa can be S, A or Q
<220> FEATURE:
<221> NAME/KEY: misc_feature
<222> LOCATION: (5)..(5)
<223> OTHER INFORMATION: Xaa can be G, D, F, W, or N
<220> FEATURE:
<221> NAME/KEY: misc_feature
<222> LOCATION: (6)..(6)
<223> OTHER INFORMATION: Xaa can be K, R, M, S, or A
<220> FEATURE:
<221> NAME/KEY: misc_feature
<222> LOCATION: (7)..(7)
<223> OTHER INFORMATION: Xaa can be A, V, or Q
<220> FEATURE:
<221> NAME/KEY: misc_feature
<222> LOCATION: (8)..(8)
<223> OTHER INFORMATION: Xaa can be V, or I
```

-continued

```
<220> FEATURE:
<221> NAME/KEY: misc_feature
<222> LOCATION: (10)..(10)
<223> OTHER INFORMATION: Xaa can be Y, H, or R

<400> SEQUENCE: 31

Xaa Gly Cys Xaa Xaa Xaa Xaa Xaa Cys Xaa Thr
1               5                   10
```

MULTIPLE ANTIGENIC PEPTIDE ASSAY FOR DETECTION OF HIV OR SIV TYPE RETROVIRUSES

CROSS REFERENCE TO RELATED APPLICATION

This is a continuation application of U.S. application Ser. No. 10/552,182, filed Oct. 5, 2005, now abandoned which is the U.S. National Stage of International Application No. PCT/US2004/011022, filed Apr. 8, 2004, which was published in English under PCT Article 21(2), and which claims the benefit of U.S. Provisional Application No. 60/462,071, filed Apr. 11, 2003. The entire disclosures of the prior applications are considered to be part of the disclosure of the accompanying application and are hereby incorporated by reference.

FIELD

This invention concerns assays for the detection of primate immunodeficiency viruses.

BACKGROUND

Human immunodeficiency virus (HIV) is subdivided into 2 types, HIV-1 and HIV-2, both of which are believed to be the result of separate zoonotic transmissions on at least eight different occasions (Hahn et al., *Science* 287:607-17, 2000; Sharp et al., *Philos Trans R Soc Lond B Biol Sci* 356:867-6, 2001) from chimpanzees and sooty mangabeys, respectively (Huet et al., *Nature* 345:356-359, 1990; Gao et al., *Nature* 397:436-441, 1999; Hirsch et al., *Nature* 339:389-392, 1989). While the origin of HIV-1 from chimpanzees is mainly supported by the phylogenetic clustering of HIV-1 and SIVcpz, substantial evidence supports the zoonotic origin of HIV-2, including similarity in the viral genome organization, phylogenetic relatedness, prevalence in the natural host, geographic coincidence and plausible route of transmission (Sharp et al., *Philos Trans R Soc Lond B Biol Sci* 349:41-47, 1995).

There is no evidence that the other lineages of simian immunodeficiency virus (SIV) have crossed into humans. The other lineages include: the SIVagm from four species of African green monkeys; the SIVsyk from sykes' monkeys; the SIVmnd from a mandrill together with SIVlhoest from l'Hoest monkeys and SIVsun from Sun-tailed monkeys; and the SIVcol from a colobus monkey. SIVs from other non-human primates from Africa have been partially sequenced and may represent new lineages. Continued study of SIV is critical for elucidating the origin and spread of HIV in humans, and monitoring future viral threats to humans.

A number of studies have provided serological evidence (using commercially available HIV tests) of SIV infections in at least 30 African non-human primates to date with viral molecular evidence in 24 of the infections (Hahn et al., *Science* 287:607-617, 2000; Lowenstine et al., *Int J Cancer* 38:563-574, 1986; Nicol et al., *J Med Primatol* 18:227-236, 1989; Peeters et al, *Emerg Infect Dis* 8:451-457, 2002). Humans are also now being increasingly exposed to the many different SIVs in different species of wild primates, for example through the hunting and butchering trade in Sub-Saharan Africa, particularly in Cameroon. This increasing human exposure to the plethora of SIVs prevalent in different species of wild primates may lead, or has already led, to additional transmissions of SIVs with the potential to cause new epidemics. Unfortunately, new zoonotic transmissions may easily go undetected because of the lack of SIV-specific tests.

There is no commercially available test specifically designed for detecting all known SIVs. Serological detection of SIVs has so far been done using HIV tests (Tsujimoto et al., *Nature* 341:539-541, 1989; Peeters et al., *AIDS* 6:447-451, 1992; Peeters et al, *AIDS Res Hum Retroviruses* 10:1289-1294, 1994; Georges-Courbot et al., *J Virol* 72:600-608, 1998; Beer et al, *J Virol* 73:7734-7744, 1999; Hirsch et al., *Virol* 73:1036-1045, 1999; Osterhaus et al, *Virology* 260:116-124, 1999) based on some cross reactivities observed with SIV antibodies to some HIV antigens. It has not been established whether all SIV strains could be detected in this way and as such, some can readily be missed (Simon et al., *AIDS Res Hum Retroviruses* 17:937-952, 2001; Peeters et al., *Emerg Infect Dis* 8:451-457, 2002) due to the high genetic diversity among primate lentiviruses. Indeed, some seronegative monkeys have been found to be infected only as determined by PCR and sequencing (Peeters et al., *Emerg Infect Dis* 8:451-457, 2002). It would therefore be useful to develop and implement testing methods and strategies sensitive and specific enough to detect diverse SIV strains in monkeys and humans in the event of zoonotic jumps to identify primary infection and prevent secondary transmission that could lead to yet another HIV-like epidemic.

SUMMARY OF THE DISCLOSURE

Disclosed herein is a method for detecting a primate immunodeficiency virus (PIV) infection by analyzing a biological sample (such as a serum sample) from a test subject to detect the presence of anti-PIV antibodies in the biological sample. The method includes contacting a biological sample with (i) at least one detection multiple antigenic peptide (MAP) from an immunodominant ("IDR") region of a transmembrane envelope protein of a primate immunodeficiency virus and (ii) at least one differentiation multiple antigenic peptide from a third variable loop ("V3-loop") of an envelope protein of a primate immunodeficiency virus. At least one of the detection (IDR) MAP or the differentiation (V3-loop) MAP can form an immune complex with primate immunodeficiency virus-specific antibody present in the biological sample. The resulting immune complex then is detected, wherein formation of the complex with the detection MAP indicates infection with a PIV, and formation of the complex with the differentiation MAP indicates infection with a particular type of PIV (such as HIV-1, HIV-2, SIVcpz, SIVsm, etc.).

Also disclosed is an enzyme immunoassay that includes a first substrate to which is bound at least one detection MAP and a second substrate to which is bound at least one differentiation MAP. The enzyme immunoassay may be provided in the form of arrays of different detection MAPs and different differentiation MAPs.

Diagnostic kits that include the detection MAP, the differentiation MAP, and instructions for performing an enzyme immunoassay of a biological sample using the detection MAP and the differentiation MAP to detect at least one primate immunodeficiency antibody in the biological sample are also described herein.

BRIEF DESCRIPTION OF THE DRAWINGS

Certain examples will be described in more detail below with reference to the following drawings.

DETAILED DESCRIPTION OF SEVERAL EXAMPLES

Figure 1:
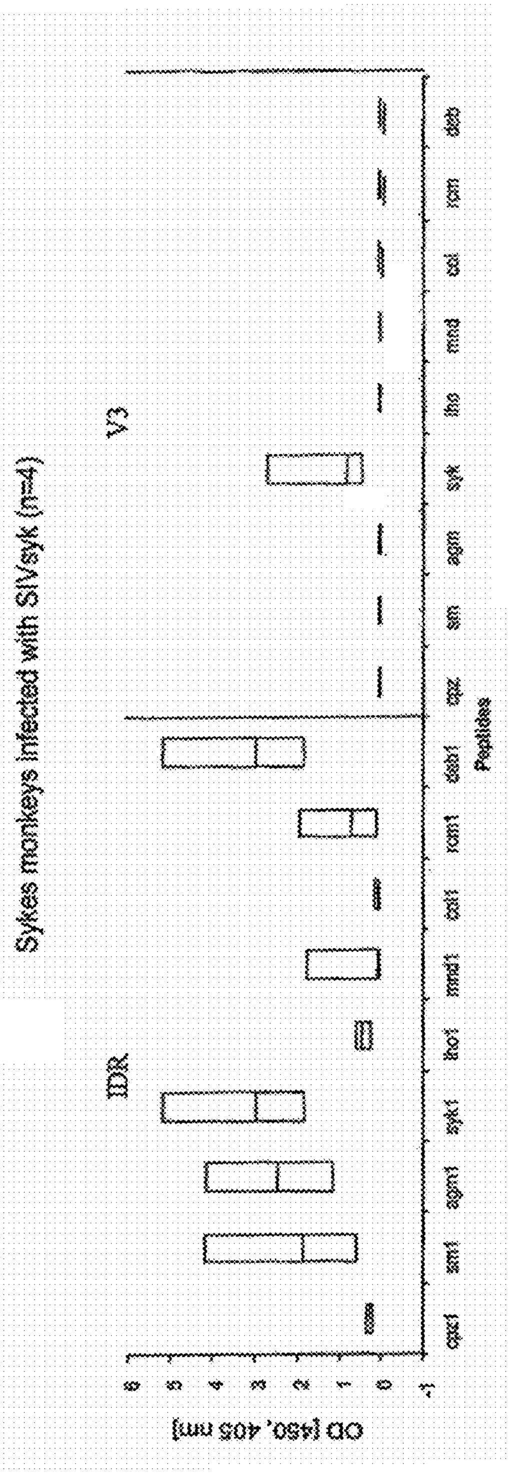
FIG. 1 is a graph showing the optical density (OD) results for an enzyme immunoassay performed on samples from Sykes monkeys infected with SIVsyk against an array of different SIV MAPs as described herein that utilized both a detection component (identified in FIG. 1 as "IDR") and a differentiation component (identified in FIG. 1 as "V3")

For ease of understanding, the following terms used herein are described below in more detail:

"Detection component" generally refers to an assay component that can detect the presence of a PIV, especially SIV.

"Diagnostically effective amount" means the amount of detectably labeled specific binding agent (e.g., a MAP that binds a PIV antibody) that, when utilized, is in sufficient quantity to enable detection of the PIV antibody.

"Differentiation component" generally refers to an assay component that can differentiate between types, strains, or sub-strains of PIV, especially SIV.

"Epitope" generally refers to any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"HIV" is the "Human Immunodeficiency Virus", which is the infectious pathogen associated with AIDS (Acquired Immunodeficiency Syndrome). "SIV" is the "Simian Immunodeficiency Virus" that is associated with a similar syndrome in macaque monkeys that have been infected with cross-species transmission. However, simian hosts that harbor naturally occurring SIV strains are asymptomatic. HIV-1 and HIV-2 are believed to have originated in non-human primates, and have been passed to humans by zoonotic transmission. The viruses that initiate infection are usually transmitted in the blood, semen or other body fluid of the infected individual. The HIV or SIV genome has the basic arrangement of nucleic acid sequences characteristic of all known retroviruses. Long terminal repeats (LTRs) at each end of the genome regulate viral integration into the host genome, viral gene expression and viral replication. The gag sequence encodes core structural proteins, and the env sequences encode the envelope glycoproteins which are required for infection of the cells. The pol sequences encode reverse transcriptase, integrase, and protease enzymes required for viral replication. The functions of these and other retroviral genes are described in great detail in Abbas et al., *Cellular Immunology,* $4^{th}$ edition, pages 454-467 (2000).

In PIV, Env is a complex that includes a transmembrane gp41 or gp36 (e.g., "gp41/gp36") subunit and an external, noncovalently associated gp120 subunit. The Env complex is expressed as a trimeric structure of three gp120/gp41 pairs that mediates a multistep process of fusion of the virion envelope with the membrane of a target CD4 positive T-cell. In some PIVs, the gp41 subunit is truncated to a gp36 subunit.

"Gp41/gp36" denotes the retroviral transmembrane envelope glycoprotein 41 or glycoprotein 36 that is found in retroviruses such as PIV. With respect to PIVs, gp 41 or gp36 is a highly immunogenic protein which elicits a strong and sustained antibody response in individuals infected with HIV. A significant proportion of the antibody response to gp41/gp36 is directed toward a well-characterized immunodominant region (IDR) within gp41/gp 36. The core of the fusion-active gp41 is composed of a trimer of two interacting peptides that contain a 36-residue peptide (N-36) and a 34-residue peptide (C-34), as described more fully in U.S. Pat. No. 6,150,088.

"Gp120" denotes the outer envelope protein found in retroviruses such as

HIV and SIV. The envelope protein is initially synthesized as a longer precursor protein of 845-870 amino acids in size, designated gp160. Gp160 forms a homotrimer and undergoes glycosylation within the Golgi apparatus. It is then cleaved by a cellular protease into gp120 and gp41. Gp41 contains a transmembrane domain and remains in a trimeric configuration; it interacts with gp120 in a non-covalent manner. Gp120 contains most of the external, surface-exposed, domains of the envelope glycoprotein complex, and it is gp 120 which binds both to the cellular CD4 receptor and to the cellular chemokine receptors (e.g., CCRS).

The gp120 core has a unique molecular structure that includes two domains: an "inner" domain (which faces gp41) and an "outer" domain (which is mostly exposed on the surface of the oligomeric envelope glycoprotein complex). The two gp120 domains are separated by a "bridging sheet" that is not part of either domain. Binding to CD4 causes a conformational change in gp120 which exposes the bridging sheet and may move the inner and outer domains relative to each other. The CD4-binding pocket within gp120 comprises a number of residues which interact directly with Phe43 of CD4. The most important of these are Glu370, Trp427 and Asp368 (the latter residue also forms a salt bridge with Arg59 of CD4). These three residues are conserved in all primate lentiviruses.

One region which has been shown to elicit neutralizing antibodies is the hypervariable V3 loop or region (V3) of the gp120; this is an epitope that elicits potent neutralizing Abs in man and experimental animals (summarized in Javaherian et al., *Science* 250:1590-93, 1990). The highly variable V3 loop of the surface protein distinguishes among PIV lineages. The V3 loop may be defined by two cysteine residues that form a disulfide bond forming the loop structure. The full length V3 sequence typically contains 33-35 amino acid residues. Examples of at least partial sequences or sub-sequences for the V3 of gp120 are NNTRGEVQIGPGMTFYNIENVVGDTRSA (SIVcpzGab) (SEQ ID NO: 23), NRSVVSTPSATGLLFYHGLEPGKNLKKG (SIVmnd) (SEQ ID NO: 24), NKTVLPVTIMAGLVFHSQKYNTRLRRQA (SIVagm) (SEQ ID NO: 25), and NKTVLPVTIMSGLVFHSQPINERPKQA (SIVsm) (SEQ ID NO: 26) (Simon et al., *AIDS Res Hum Retroviruses* 17:937-952, 2001). Further examples of V3 sequences can be found in Pau et al., *AIDS Research and Human Retroviruses,* 10:1369-1377, 1994).

"Immunodominant region" or "IDR" refers to the subunit of an antigenic determinant that elicits a strong immunological response. It has been established by use of chemical synthetic peptides that the IDR epitopes of HIV-1 or HIV-2 envelope proteins are located in the relatively conserved regions. An example of the location of the IDR for certain strains of HIV-1 gp41 is at amino acid positions 584-618 (Shin et al., *Biochemistry and Molecular Biology International* 43:4:713-721, 1997), and, more particularly, at 598-609 (Gnann et al., *Journal of Virology* 61:2639-2641, 1987). An example of a location of the IDR for HIV-2 gp36 is at amino acid positions 574-602 (Shin et al., *Biochemistry and Molecular Biology International* 43:4:713-721, 1997). The IDRs of the various SIVs are at the same or similar positions. The full length sequence of the IDR of gp41/gp 36 typically contains 34-44 amino acid residues. Examples of at least partial sequences or sub-sequences for the IDR of gp41/gp36 are LAVERYLQDQQILGLWGCSGKAVC (SIVcpzGab) (SEQ ID NO: 27), TSLENYIKDQALLSQWGCSWAQVC (SIVmnd) (SEQ ID NO: 28), TALEKYLEDQARLNIWGCAFRQVC (SIVagm) (SEQ ID NO: 29), and TAIEKYLKDQAKLNSWGCAFRQVC (SIVsm) (SEQ ID NO: 30) (Simon et al., *AIDS Res Hum Retroviruses* 17:937-952, 2001).

"Multiple antigen peptide" refers to a combination antigen/antigen carrier that is composed of two or more, identical or different, antigenic molecules. In some instances, the antigenic molecules are covalently attached to a dendritic core that is composed of bifunctional units, such as lysine molecules. For example, a lysine is attached via peptide bonds through each of its amino groups to two additional lysines. This second generation molecule has four free amino groups each of which can be covalently linked to an additional lysine to form a third generation molecule with eight free amino groups. A peptide may be attached to each of these free groups to form an octavalent multiple peptide antigen. Alternatively, the second generation molecule having four free amino groups can be used to form a tetravalent MAP. In other examples, aspartic acid or glutamic acid can be used to form the dendritic core of a multiple peptide antigen. The dendritic core, and the entire MAP, may be conveniently synthesized on a solid resin using the classic Merrifield synthesis procedure.

"Peptide" refers to any molecule or moiety comprising two or more amino acid residues joined to each other by peptide bonds or modified peptide bonds, i.e., peptide isosteres. Peptides may contain amino acids other than the 20 gene-encoded amino acids. Peptides include amino acid sequences modified either by natural processes, such as post-translational processing, or by chemical modification techniques. Glycosylated and non-glycosylated forms of peptides are also embraced by "peptides." Peptides can include D or L-amino acid residues. "Peptides" also includes peptide analogues such as synthetic constructs using the carbon skeleton of peptides but omitting the -CONH- peptide bonds.

"PIV" is a primate immunodeficiency virus, which includes both HIV and SIV, for example the human viruses HIV-1 and HIV-2; the chimpanzee virus SIVcpz such as, for example, SIVcpzGab, SIVcpzCam, SIVcpzAnt, and SIVcpzUS; the sooty mangabey virus SIVsm; the African green monkey virus SIVagm such as, for example, SIVagm-1 and SIVagm-2; the mandrill virus SIVmnd such as, for example, SIVmnd14 and SIV mndGB 1, as well as a host of others including SIVsun/lhoest, SIVcol, SIVrcm, SIVsyk, SIVdeb, SIVgsn, SIVmon, SIVmus, and SIVtal. PIV is inclusive of all strains (e.g., SIVcpz) and sub-strains (e.g., SIVcpzGab).

"PIV antibody detection specificity" refers to the capability of an assay to detect true PIV-negative biological samples (i.e., accurately differentiate between PIV-positive and PIV-negative biological samples). For example, specificity is expressed herein in the terms of true-negative test results divided by all subjects not infected with the virus. In other words, specificity=(d/(b+d)) wherein d=true negatives and b=false positives. An increase in the specificity of an assay results in fewer false positives.

"PIV antibody detection sensitivity" refers to the capability of an assay to detect true PIV-positive biological samples. For example, sensitivity is expressed herein in the terms of true-positive test results divided by all subjects infected with the virus. In other words, sensitivity=(a/(a+c)) wherein a=true positives and c=false negatives. An increase in the sensitivity of an assay results in fewer false negatives.

"Sequence identity" refers to the similarity between two nucleic acid sequences, or two amino acid sequences, and is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of a peptide sequence (such as the sequence of an IDR of gp41/36 or the V3 peptide), and the corresponding DNA sequence, will possess a relatively high degree of sequence identity when aligned using standard methods. This homology will be more significant when the orthologous proteins or DNAs are derived from species which are more closely related (e.g., human and chimpanzee sequences), compared to species more distantly related (e.g., human and murine sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-244, 1988); Higgins & Sharp, *CABIOS* 5:151-153, 1989; Corpet et al., *Nuc. Acids Res.* 16, 10881-90, 1988; Huang et al., *Computer Appls. in the Biosciences* 8, 155-65, 1992; and Pearson et al., *Meth. Mol. Bio.* 24, 307-31, 1994. Altschul et al., *J. Mol. Biol.* 215:403-410, 1990, presents a detailed consideration of sequence alignment methods and homology calculations.

The NCBI Basic Local Alignment Search Tool (BLAST) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity using this program. BLAST searching permits determination of sequence identity between a given sequence, for example, a nucleotide sequence, and a reference sequence. Nucleotide sequences with increasing similarity to a reference sequence show increasing percentage identities, for example at least 50%, at least 70%, at least 80%, at least 85%, at least 90%, at least 95%, or at least 98%.

Homologs of the disclosed peptides typically possess at least 60% sequence identity counted over full-length alignment with the reference sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described in the NCBI website. These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (1989) *Molecular Cloning: A Laboratory Manual*, CSHL, New York and Tijssen (1993) *Laboratory Techniques in Biochemistry and Molecular Biology—Hybridization with Nucleic Acid Probes* Part I, Chapter 2, Elsevier, N.Y. Nucleic acid molecules that hybridize under stringent conditions to a given sequence will typically hybridize under wash conditions of 2×SSC at 50° C.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

The above term descriptions are provided solely to aid the reader, and should not be construed to have a scope less than that understood by a person of ordinary skill in the art or as limiting the scope of the appended claims.

The immunoassay disclosed herein is useful for detecting primate immunodeficiency viruses (PIV) in a biological sample. The immunoassay is especially useful for detecting SIV in non-human primates and SIV-like infections in humans. The assay also is useful for detecting previously unrecognized SIV-like retroviruses in humans and non-human primates. Furthermore, the assay can be used for differentiating between specific SIV strains.

The assay method generally involves contacting the biological sample with multiple antigenic peptides (MAPs) from an immunoreactive region of PIV envelope proteins. The biological sample is contacted with the MAPs under conditions which are suitable for forming immune complexes between PIV-specific antibodies in the biological sample and the MAPs. The assay can detect a wide variety of PIVs by providing an array of MAPs from multiple PIVs, wherein the MAPs for each PIV include a detection component and a differentiation component. Of course, certain examples of the assay may include only the detection component or differentiation component for a given specific PIV. In a particular example, the detection component is an IDR peptide of a PIV transmembrane protein (for example, from gp41 or gp 36), and the differentiation component is a V3 peptide of an envelope protein (for example, gp120). The IDR component provides a high degree of sensitivity to antibodies against many PIV strains, while the V3 component is a less sensitive, but more specific variable component that differentiates between PIV species. Certain examples of the IDR peptide and the V3 peptide have sequence lengths that are set forth below in order to enhance their specificity for PIV, particularly SIV. In addition, the MAP construct provides an assay with a significantly improved degree of analytical sensitivity as detailed below.

The presently described methods are particularly useful for serological testing employing serum or plasma samples, although the biological samples could alternatively be in the form of any body fluid such as whole blood, urine, saliva and other fluids or body tissue. The biological samples can be taken from humans, non-human primates, and experimental animal models such as mice or rabbits.

MAPs, which are described in more detail below, typically include peptide antigen sequences covalently linked to a branching, dendritic core residue or matrix composed of bifunctional units (e.g., lysines). More specifically, a biological sample is contacted with at least one first MAP that serves as a detection component (for example, a MAP from an immunodominant region of a transmembrane protein of a PIV) and at least one second MAP that serves as a differentiation component (for example, a MAP from a V3-loop of an envelope protein of a PIV). The first MAPs in these examples are referred to herein as "IDR MAPs" and the second MAPs are referred to herein as "V3 MAPS."

The assaying of a sample from an individual subject with the IDR and V3 MAPs may be performed serially or simultaneously. If performed serially, the assaying can be conducted in any order. In other words, a first portion of a biological sample from an individual subject may be contacted with the IDR MAPs. A second portion of the same biological sample may be contacted with the V3 MAPs, either simultaneously, prior to, or after, the IDR assaying. In certain variations, IDR and V3 testing could be performed simultaneously by providing IDR and V3 MAPs on the same panel or microplate.

The MAP assays also can be used to quantify anti-PIV antibodies in sera, measure the affinity of the antigen-antibody complex, or the avidity of the antigen-antibody complex. Such measurements can be obtained by using techniques known in the art.

Specific examples of MAPs that are useful in the presently disclosed assay are composed of two or more, usually identical, antigenic peptides covalently attached to a dendritic core matrix which is composed of bifunctional units. Suitable core molecules for constructing MAPs include ammonia, ethylenediamine, aspartic acid, glutamic acid and lysine. For example, a lysine core molecule is attached via peptide bonds through each of its amino groups to two additional lysines. This second generation molecule has four free amino groups, each of which can be covalently linked to an additional lysine to form a third generation molecule with eight free amino groups. A peptide may be attached via its C-end to each of these free groups to form an octavalent multiple antigenic peptide (also referred to as a "MAP8" structure). Alternatively, the second generation molecule having four free amino groups can be used to form a tetravalent or tetrameric MAP, i.e., a MAP having four peptides covalently linked to the core (also referred to as a "MAP4" structure). The carboxyl group of the first lysine residue may be left free, amidated, or coupled to β-alanine or another blocking compound. As used herein, the "linear portion or molecule" of a MAP system structure refers to the antigenic peptides that are linked to the core matrix. Thus, a cluster of antigenic epitopes form the surface of a MAP and a small matrix forms its core.

The dendritic core, and the entire MAP may be conveniently synthesized on a solid resin using a classic Merrifield synthesis procedure. MAP synthesis, is generally described, for example, in U.S. Pat. Nos. 5,580,563, and 6,379,679, and Tam, *Proc. Natl. Acad. Sci. USA* 85:5409-5413, 1988.

Examples of a schematic structure of a tetrameric or MAP4 peptide are represented below in Formula 1

Formula 1

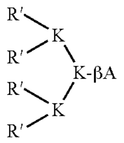

wherein R' represents an amino acid sequence, especially a linear sequence. Each R' may be the same or different. The number of amino acid residues in R' may vary, and is described in more detail below.

A comprehensive array of peptides covering gp41/36 and gp120 proteins regions of all recognized (i.e. characterized) SIV strains can be used. The assay is an open-ended assay in that new MAPs can be added to the assay template as additional SIV strains are identified and characterized. Consequently, the assay has the flexibility to be contemporaneously updated so that it may be capable of screening for all SIV strains recognized or known at the time of assaying. Of course, variants of the assay can be made with less than all of the known SIV strains. According to one example, the assay does not include any peptides from HIV (in other words, the assay only includes peptides from SIV).

The specific MAPs may be arranged in any suitable configuration in the array. For example, the MAPs may be bound onto an 8×12 microwell plate in which a first MAP (e.g., a MAP from SIVcpzGab) is coated into all the wells in the first column, a second MAP (e.g., a MAP from SIVsm), is coated into all the wells in the second column and so forth.

Antibodies generally cannot bind to the whole antigen molecule. Generally, a specific antibody binds specifically to one individual epitope on a protein antigen. In the presently disclosed assays, the antigenic reactive substance is from certain immunodominant epitopes. More specifically, the antigenic peptide R' sequences in the MAPs are selected from immunodominant regions in the respective native transmembrane or envelope proteins. As mentioned above, the R' antigen peptides may be the same or different in individual MAP molecules. Employing different R' antigen peptides in individual MAP molecules can allow for the inclusion of a wider variety of PIVs in a single assay.

Peptides from all primate lentiviral lineages for which envelope sequences were available at the time of preparing the provisional patent application from which the present application claims priority were used in one example of the assay. The peptides were those that can be expressed from 2 separate regions of the envelope protein of the viral genome. The first region was the immunodominant region (IDR) of the transmembrane protein (gp41/gp36), and the second region was the V3-loop of the envelope protein (gp120). As described above, the IDR epitope was selected for its high sensitivity and the V3-loop was selected for its high specificity. The detection component and/or the differentiation component also could be from other regions of the envelope, gag, or pol protein.

Given that longer peptides may give rise to non-specific reactivities outside or within primate lentiviruses, especially useful peptide sequences for MAP synthesis and assaying have less than about 16 amino acid residues per linear portion of each MAP. In illustrative examples, each linear portion of each IDR MAP may include about 5 to about 15, more particularly about 7 to about 11, amino acid residues, and each linear portion of each V3 MAP may include about 5 to about 15, more particularly about 7 to about 15, amino acid residues. Peptide sequences of such lengths are particularly useful for constructing MAPs from SIV strains. It should be recognized that the number of amino acid residues provided above does not include any non-viral coded amino acid residues that may be used as spacers in the R' linear portion of a MAP such as that depicted above in Formula 1.

The R' sequences for the IDR MAP may be selected, for example, from the IDR sequences discussed above such as SEQ ID NOS: 27-30. Especially useful R' sequences for the IDR MAP are those that contain a minimum of 7 amino acid residues defined by two cysteine residues. According to one example of the detection MAP, the R' sequence of the IDR MAP construct may have (or include) a consensus sequence represented by (SEQ ID NO: 31)

$$X_1GCX_4X_5X_6X_7X_8CX_{10}T$$

wherein $X_1$ is W, I or F;
$X_4$ is S, A or Q;
$X_5$ is G, D, F, W or N;
$X_6$ is K, R, M, S, or A;
$X_7$ is A, V or Q;
$X_8$ is V, or I; and
$X_{10}$ is Y, H or R.

Alternatively, the R' sequence of the detection MAP is SEQ ID NOS: 1, 8, 9, or a sequence having at least 80%, 90% or 95% sequence identity to one or more of those sequences.

The R' sequences for the V3 MAP may be selected, for example, from the V3 sequences discussed above such as SEQ ID NOS: 23-26. In an example of the differentiation MAP, R' is one or more of SEQ ID NOS: 14-22, or a sequence having at least 80%, 90% or 95% sequence identity to one more of those sequences.

One illustrative MAP array used in an example of the presently described assay is shown below in Table 1.

TABLE 1

Composition of IDR and V3 peptides used in a MAP assay.

| Virus | IDR gp41/36 peptides | SEQ ID NO: | Virus | V3 peptides | SEQ ID NO: |
|---|---|---|---|---|---|
| SIVcpzGab | WGCSGKAVCYT | 1 | SIVcpzGab | RGEVQIGPGMTFYNI | 14 |
| SIVcpzCam | WGCSGKAICYT | 2 | SIVsm | VLPVTIMSGLVFHSQ | 15 |

TABLE 1-continued

Composition of IDR and V3 peptides used in a MAP assay.

| Virus | IDR gp41/36 peptides | SEQ ID NO: | Virus | V3 peptides | SEQ ID NO: |
|---|---|---|---|---|---|
| SIVcpzAnt | WGCADKVICHT | 3 | SIVagm | LPVTIMAGLVFHSQ | 16 |
| SIVsm | WGCAFRQVCHT | 4 | SIVsyk | IKNIQLAAGYFLPVI | 17 |
| SIVagm-1 | WGCAWKQVCHT | 5 | SIVlhoest | EVSTISSTGLLFYYG | 18 |
| SIVagm-2 | WGCAFKQVCHT | 6 | SIVcol | HRNLNTANGAKFYYE | 19 |
| SIVsun/lhoest | WGCQWKQVCHT | 7 | SIVrcm | VKGISLATGVFISLR | 20 |
| SIVcol | IGCANMQICRT | 8 | SIVmnd14 | IVSVPSASGLIFYHG | 21 |
| SIVrcm | FGCAWRQVCHT | 9 | SIVdeb | YRAVHMATGLSFYTT | 22 |
| SIVmnd14 | WGCSFSQVCHT | 10 | | | |
| SIVmndGB1 | WGCSWAQVCHT | 11 | | | |
| SIVsyk | WGCAFKQICHT | 12 | | | |
| SIVdeb | WGCAFKQICHT | 13 | | | |

An array of the specific MAPs shown in Table 1 is immobilized on a microtiter plate as described in more detail below. The sequences listed represent specific examples of the R' group of Formula 1. In the case of an IDR MAP, each R' also includes β-alanine (βA) and d-aspartic acid (dD) between the specific epitope sequence listed in Table 1 and each lysine matrix molecule (e.g., SEQ ID NO: 1-βA-dD-K-). The β-alanine (βA) residue serves as a spacer amino acid between the reactive epitope sequence and the lysine core. The d-aspartic acid (dD) residue serves as a spacer amino acid and improves the solubility of the MAP. Lysine and glutamic acid also can be used as spacer amino acids. In the case of a V3 MAP, each R' also includes diaminopropionic acid (X) as a spacer amino acid between the specific epitope sequence listed in Table 1 and each lysine matrix molecule (i.e., SEQ ID NO: 14-X-K-). As an example, Formulae 2 and 3 show specific MAP structures with SEQ ID NO: 1 and SEQ ID NO: 14, respectively.

Formula 2

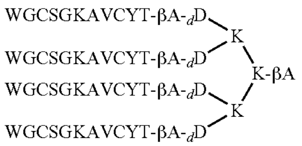

Formula 3

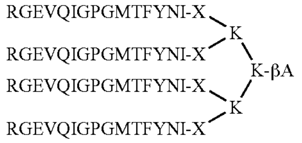

The specificity of peptides generally tends to increase as the length of the peptides decreases, but shorter peptides may also have reduced reactivity, which can reduce the sensitivity of the test. The MAP structure can compensate for this reduced sensitivity. In particular, the plurality of shorter linear peptides in the presently disclosed MAPs enables optimization for specificity and sensitivity. The specificity is enhanced by shorter linear peptide portions that are more antigenicity focused. The sensitivity is enhanced by the plurality of shorter linear peptides. For instance, the analytical discernability of the assay results is increased (e.g., the optical density readout exhibits a more intense color). Although not bound by any theory, it is believed that since only a portion of the MAP molecule is in contact with the solid phase substrate, the other portions of the MAP molecule are free for antibody binding. In addition, MAPs provide increased antigen density, and thus an increased number of antibody binding sites per unit surface area.

The PIV antibody detection specificity of the presently disclosed assays may be, for example, at least about 95%, and more particularly substantially 100%. The PIV antibody detection sensitivity of the presently disclosed assays may be, for example, at least about 95%, and more particularly substantially 100%. When IDR and V3 components are used in combination, 100% specificity and sensitivity may be achieved.

The MAPs may be contacted with a biological sample by any suitable assay technique. For instance, the MAPs may be bound to a solid phase substrate that is then contacted with the biological sample. The solid phase substrate could be a microtiter plate in which each specific MAP is bound to an individual microwell. Alternatively, the MAPs could be bound to solid beads, magnetic beads or similar type of particulate media, membranes, discs, gels, flat sheets, test strips, fibers and other configurations and types of materials that permit antigens to be attached to the support. Attachment may be made by non-covalent or covalent means. Preferably, attachment will be made by adsorption of the antigen to a well in a microtiter plate, a membrane such as nitrocellulose, or latex beads. Other possible attachment techniques include biotinylation of the MAPs and capture of the MAPs with avidin on a solid phase. A diagnostically effective amount of MAP is coated onto the solid phase substrate. Such an amount may range, for example, from about 0.1 to about 1 μg. A single MAP, or a mixture of different MAPs, may be coated in each well.

One optional approach contemplates providing a first solid phase substrate that includes an array of desired IDR MAPs, and a second solid phase substrate that includes an array of desired V3 MAPs. Serum sample(s) from an individual subject then are contacted to both the IDR MAP substrate and the V3 MAP substrate. In another optional approach, IDR MAPs and V3 MAPs are arrayed on a single solid phase substrate and a serum sample is flowed over, around, and/or through the substrate such that the sample contacts both the IDR MAPs and the V3 MAPs. According to a further optional approach IDR MAPs and V3 MAPs can be mixed together, and the resulting mixture is coated on individual wells.

Any type of immunologic method or methods may be employed to detect the formation of an immune complex between the IDR MAP and/or V3 MAP and PIV-specific antibody present in the biological sample. Illustrative techniques include radioimmunoassays, competitive immunoassays, enzyme immunoassays (EIA) such as enzyme-linked immunosorbent assays (ELISA), immunoflourescence, and lateral flow immunoassays. In general, once the biological sample is exposed to the immobilized MAPs for a sufficient time (e.g., about 10 minutes to about 24 hours), the support is washed to eliminate any material from the biological sample that is not bound to the MAPs. Such washing step(s) may be performed with saline and other additives typically included in a washing solution. A labeled reagent then is added to the material on the solid support to detect the binding between the MAPs on the solid support and PIV-specific antibody in the biological sample. Such a reagent may be an anti-human immunoglobulin, such as goat anti-human immunoglobulin, protein A or protein G or any anti-animal immunoglobulin. In one example, the label can be a colorimetric indicator which upon contact with a substrate produces a detectable color signal. The presence and/or intensity of the color provides evidence of the presence of the antibody. Other labels or reporter groups include a radioisotope, a fluorescent compound, a fluorescence emitting metal of the lanthanide series, a chemiluminescent or phosphorescent molecule, a paramagnetic group, or an enzyme.

The methods disclosed herein are particularly useful with ELISA. In general, ELISA involves immobilizing an IDR MAP or V3 MAP onto a solid phase substrate (e.g., a microwell or microtiter plate). Sera or plasma are added to the microwells, and then the microwells are washed to remove unbound antibody. A second antibody, which is an anti-human immunoglobulin (or any anti-animal immunoglobulin) antibody linked with an enzyme, is then added to the wells. Then the substrate for the enzyme is added to the washed well and the amount of enzymatically altered substrate is measured. The enzyme and substrate are chosen so that enzymatic modification of the substrate produces a change in color of the substrate solution. The amount of changed substrate (which may be measured with a spectrophotometer) as a result of the enzyme-antibody-antigen reaction is proportional to the amount of antibody bound to the immobilized MAPs (i.e., the formation of antigen-antibody complex). Illustrative enzymes include alkaline phosphatase, glucose oxidase, beta-galactosidase, catalase, malate dehydrogenase, horseradish peroxidase, yeast alcohol dehydrogenase, and similar enzymes. The assay can be performed using automated ELISA processing equipment such as those instruments commercially available from Grifols-Quest, Inc. or Axsyn.

By recording or tracking the coordinates of each specific MAP immobilized on the microplate, which PIV-specific MAP(s) that have formed immune complexes can be determined. Thus, the assay disclosed herein can also differentiate between specific PIV strains.

As mentioned above, the assays disclosed herein can also be utilized for screening for divergent SIV strains. More specifically, if a certain biological sample is positive for both the IDR and the V3 components, then the molecular structure of the sample can be further characterized by techniques such as polymerase chain reaction (PCR) and gene sequencing. The characterized molecular structure then can be compared to reference SIV strains to determine if the sample of interest is a divergent or previously unrecognized strain.

Also disclosed herein are diagnostic kits that can be used to perform the above-described detection methods. A kit could include microplates on which the desired MAPs have already been immobilized. Alternatively, the kit could include containers containing MAPs in solution for coating onto microplates by the user. Any number of different MAPs could be included, but the kit preferably would include MAPs corresponding to all the SIV recognized and characterized at the time the kit was prepared.

Also provided in the kit are containers containing labeled reagents or conjugates which detect the binding of antibody to the immobilized MAP, such as goat anti-human immunoglobulin or the like. The label on the reagent may be selected from any type of diagnostic labels, such as radioactive compounds, fluorescent compounds and proteins, colorimetric enzymes, etc. The kit also may contain miscellaneous reagents and apparatus for reading labels (e.g., certain substrates that interact with an enzymatic label to produce a color signal), apparatus for taking blood samples, as well as other appropriate vials and other diagnostic assay components. One specific example of a kit could include various MAPs, a bicarbonate buffer for dissolving the MAPs, a goat anti-human immunoglobulin conjugate, a milk buffer, phosphate-buffered saline, and an enzyme substrate such as tetramethylbenzylidene/hydrogen peroxide. Instructions for performing the assay may also be included with the kit.

The kit also could include a reference or key member having colorimetric standards corresponding to the optical densities indicating PIV-positive hits. Such a reference or key member could be used for visually detecting PIV-positive hits with the unaided eye in the event that spectrophotometry instruments are unavailable in the field. The reference member, for example, could be a paper or plastic substrate or a container having different colored regions on its surface. Each component of the kit could be packaged together or separately.

The specific examples described below are for illustrative purposes and should not be considered as limiting the scope of the appended claims.

MAP Synthesis

All the peptide sequences used in the exemplified assay are shown above in Table 1. The MAPs were synthesized using a solid-phase method, 9-fluorenyl-methoxycarbonyl (Fmoc) chemistry according to the manufacturer's protocol on an automatic synthesizer (model 432A, Applied Biosystems, Inc., Foster City, Calif.). The synthesis started from the right side of the illustrative structure shown above in Formula 1, and then proceeded to the left side through the R' sequence. After synthesis, the MAPs were partially purified by reverse phase high-performance liquid chromatography (BioRad, Richmond, Calif.), lyophilized, and stored desiccated at room temperature until use.

MAP Enzyme Immunoassay

The MAPs (10 μg/μl) were first dissolved in dimethyl sulfoxide (Aldrich Milwaukee, Wis., USA), then diluted in cold bicarbonate buffer (0.1 M, pH 9.4) to a final concentration of 0.25 μg/100 μl. The MAP solutions then were coated (110 μl/well) onto microtiter plates (Maxisorb, Nalge Nunc International, Rochester, N.Y.) at 4° C. overnight. MAPs that were derived from the same primate species or which have very close identity amino acid sequences were mixed to a maximum of two per well and then coated. In particular, the SIVcpzGab and SIVcpzCam IDR MAPs were mixed together, the SIVagm-1 and SIVagm-2 IDR MAPs were mixed together, and the SIVsyk and SIVdeb IDR MAP is the same MAP. Unbound MAP was removed by washing 2 times with phosphate buffered saline (PBS, pH 7.5) containing 0.05% TX-100 (Sigma Chemical Co., St. Louis, Mo.) (PBS-TX), dried at 37° C., sealed in bags with dessicant, and stored at -20° C. until use. Non-specific binding sites were blocked with 5% nonfat dry milk in PBS containing 0.1% Triton X-100 (milk buffer) (octylphenol ethylene oxide condensate) for 30 minutes at 37° C. just prior to performing the assay. Plasma samples were diluted 1:500 in milk buffer, and 100 μl was added to the MAP-coated well and incubated for 1 hour at 37° C. Bound antibodies were detected with 1:8000 dilution (30 minutes incubation at 37° C.) of goat anti-human IgG(H+L)-peroxidase conjugate (BioRad, Hercules, Calif.) and tetramethyl-benzydine/hydrogen peroxidase substrates (BioFX, Owings Mills, Md.) for 10 minutes at room temperature. Color development was stopped with 1M sulfuric acid and optical density (OD) was measured at 450 against a reference of 630 nm.

Reference Panels

The assay was evaluated using known and well characterized simian and human samples obtained from divergent representatives of primate species known to carry lentiviruses belonging to 6 viral lineages.

1. Non-Human Primate Reference Panel

This panel included 54 sera from various monkeys experimentally or naturally infected with SIVs, and include all SIV strains for which envelope V3 and IDR sequences were available. In general, viral DNA from a number of these samples was amplified while others were only serologically confirmed by EIA and western blot. Table 1 below shows the SIV strains included in the panel: 6 samples from sooty mangabeys, 10 from macaques (4 rhesus and 6 stumptail) accidentally infected with SIVsm, 9 from African green monkeys infected with SIVagm; 4 specimens from sykes monkeys infected with SIVsyk; 3 specimens from chimpanzees infected with SIVcpz (SIVcpzGab, SIVcpzAnt and SIVcpzUS); 2 from macaque monkeys infected with SIV1'Hoest and SIVsun; 4 from colobus monkeys infected with SIVcol; 8 from mandrills, 1 from a drill infected with SIVmnd and SIVdrl, 2 from red capped mangabeys infected with SIVrcm; 4 from talapoin monkeys infected with SIVtal, and one specimen from a De Brazza monkey likely infected with SIVdeb, based on serological results. Since the assay is intended to test humans for SIV-like infections, two specimens from humans occupationally infected with SIVsm were also included in the panel.

TABLE 2

Non human primate reference panel

| Species | Common name | Virus | SIV+ | SIV− |
|---|---|---|---|---|
| *Cercocebus atys* | Sooty mangabey | SIVsm | 6 | 6 |
| *C. torquatus* | Red-capped mangabey | SIVrcm | 2 | 15 |
| *Macaca* spp | Macaque | SIVsm | 10 | 8 |
| *Chlorocebus. pygerythrus* | Vervet monkey | SIVagmVer | 4 | 3 |
| *C. tantalus* | *Tantalus* monkey | SIVagmTan | 4 | 4 |
| *C sabaeus* | Green monkey | SIVagmSab | — | 3 |
| *Cercopithecus albogularis* | Sykes monkey | SIVsyk | 4 | 4 |
| *C. l'hoesti* | L'Hoest monkey | SIVlhoest | 2 | 1 |
| *C. neglectus* | De Brazza monkey | SIVdeb | 1 | 1 |
| *Colobus. guereza* | *Guereza colobus* | SIVcol | 4 | 32 |
| *Mandrillus. sphinx* | Mandrill | SIVmnd | 8 | 5 |
| *M. leucophaeus* | Drill | SIVdrl | 1 | 3 |
| *Myopithecus. talapoin* | *Talapoin* monkey | SIVtal | 4 | 5 |
| *Pan troglodytes troglodytes* | Cent. Africa chimpanzee | SIVcpz (p.t.t.) | 2 | 3 |
| *P. t. schweinfurthii* | East Africa chimpanzee | SIVcpz (p.t.s.) | 1 | — |
| Total | | | 54 | 93 |

To determine the specificity of the assay, 93 SIV negative sera from various monkey species (6 sooty mangabeys, 10 African green monkeys, 3 chimps, 4 Sykes, 1 1'Hoest, 5 mandrills, 3 drills, 8 macaques, 32 colobus, 5 talapoins, 15 red-capped mangabeys, and one De Brazza) were tested. Seronegative status of these monkeys was established based on the absence of reactivity to commercial ELISA immunoassays. Seventeen of these monkeys were infected with SFV, STLV.

2. Human Reference Panel

To assess the specificity of the assay for application in human testing, 198 HIV seronegative samples collected in US blood banks were tested. Specimens from the US were preferred as reference over seronegative samples from Cameroon or other parts of Africa because the close contact of humans and monkeys in this region makes African specimens inappropriate for the purpose.

To determine the reactivity of HIV-1/2 antibodies with the SIV MAPs, included in the evaluation were specimens from individuals infected with HIV. These specimens were as follows: 70 non-B HIV-1 group M from Africa, including subtypes A (n=27), C (n=1), D (n=14), AE (n=1), F (n=7), G (n=18), H (n=1) and J (n=1) in addition to 50 subtype B from the US; 4 HIV-1 group O from Cameroon; 44 HIV-2 from Nigeria and Ivory Coast; and 5 HIV-1+2 from Nigeria.

Other common African infections were also checked that might cross-react with SIV MAPs by employing specimens from individuals infected with other endemic infectious agents to evaluate any cross-reactivity with the SIV MAPs. These included 18 specimens from malaria patients infected with the 4 main species of Plasmodium: *P. falciparum* (n=4), *P. malariae* (n=2), *P. ovale* (n=5), and *P. vivax* (n=7); 44 specimens from HTLV positive individuals; 3 specimens from individuals infected with measles; and 3 specimens from individuals infected with simian foamy virus (SFV).

The MAP assay described in Table 1 was also employed to determine whether humans are becoming infected with SIV through exposure to infected nonhuman primate blood and body fluids. Three groups of HIV negative plasma samples from Cameroon were available for comparisons: from persons with a high level of exposure (HE) through hunting/butchering in remote villages (n=76), persons with a lower level of exposure (LE) in remote villages (n=77), and a general (G) population (n=1071).

Results

The results obtained from various panels of samples were analyzed using the box-plot technique. The test performance was evaluated by calculating the sensitivity and specificity.

1. Non-Human Reference Panel

Three specimens originated from chimpanzees (two *P. troglodytes schweinfurthii* and one *P. t.troglodytes*) infected with SIVcpz. All three reacted with the N and SIVcpz IDR MAPs, with one showing additional reactivity within the lineage with group M peptide. There was no reactivity with other peptides outside this lineage. One of the 2 specimens from P t. s. did not react on the V3 MAP component, which might be due to low antibody titer since the IDR reactivity was relatively lower.

Figure 2:
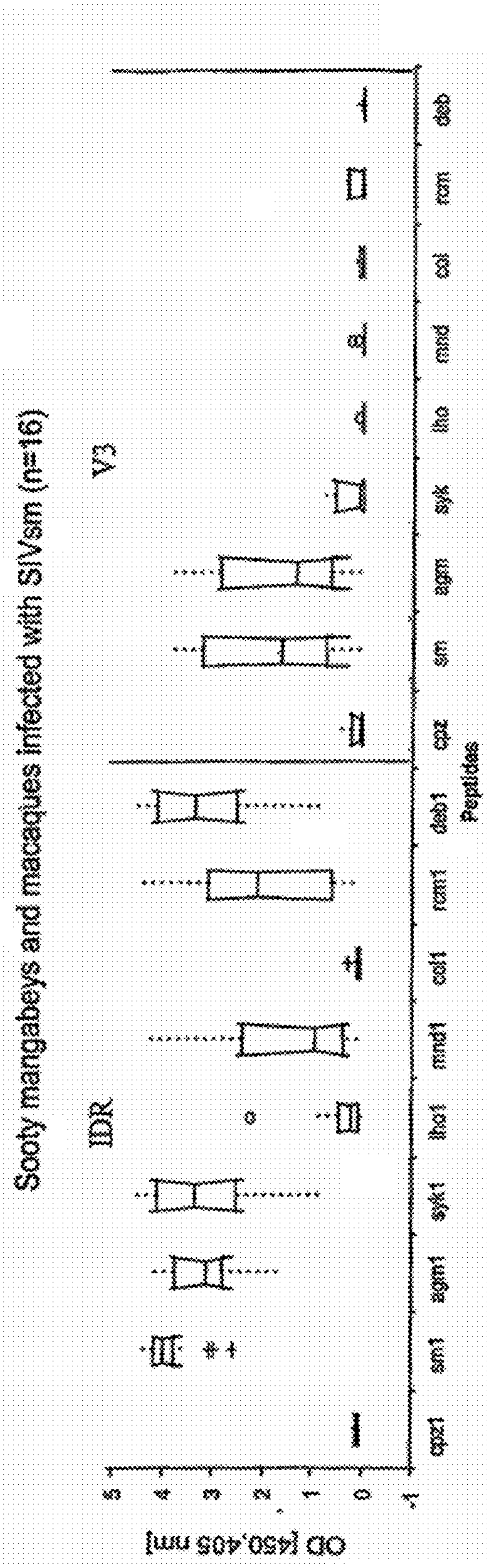
FIG. 2 is a graph showing the optical density (OD) results for an enzyme immunoassay performed on samples from sooty mangabeys and macaques infected with SIVsm against an array of different SIV MAPs as described herein that utilized both a detection component (identified in FIG. 2 as "IDR") and a differentiation component (identified in FIG. 2 as "V3")

For the second lineage (HIV-2/SIVsm), specimens from 6 sooty mangabeys and 10 macaques (Rhesus and stumptail) infected with SIVsm were used. All 16 specimens were detected in both IDR and V3 components. Although some cross-reactivity was observed in the IDR region, the V3 component showed specific reactivity only to the second lineage. The results are depicted in FIG. 2 which clearly shows the IDR cross-reactivity sensitivity and the improved specificity obtained with the V3 component. Hence the IDR identifies the presence of the PIV, and the V3 component differentiates the particular virus that is present.

The third group of simian samples consisted of 9 African green monkeys infected with SIVagm. All the specimens were determined to be positive by the assay. There were limited and low reactivity with IDR MAPs from other lineages (HIV-2/SIVsm, SIVsyk) but the highest reactivity was to the homologous MAPs. The V3 MAP was less cross-reactive and therefore more specific to the SIVagm lineage.

Five sera from infected sykes monkeys were also determined to be positive by the assay. There was some cross reactivity observed in IDR mainly with the SIVagm MAPs, as it was reversibly the case with SIVagm specimens reacting against sykes MAPs. The V3 reactivity was very specific only to sykes MAPs. The results are depicted in FIG. 1 which clearly shows the IDR cross-reactivity sensitivity and the V3 specificity.

There were only 2 SIV positive sera from l'Hoest monkeys and both were detected. Cross-reactivity was observed mainly with the HIV-2/SIVsm and AGM gp36 peptides. This is probably due to their similarity in this gene region. The V3 again was specific although one of the specimens showed cross-reactivity with HIV-1 group O peptide. Specimens from 8 mandrills and 1 drill infected with SIVmnd and SIVdrl were tested and all reacted with the homologous peptides with some cross-reactivity with HIV-2, AGM, RCM, Sykes and l'Hoest in the IDR while cross-reactivity in the V3 component was only directed to the l'Hoest peptides.

Figure 3:
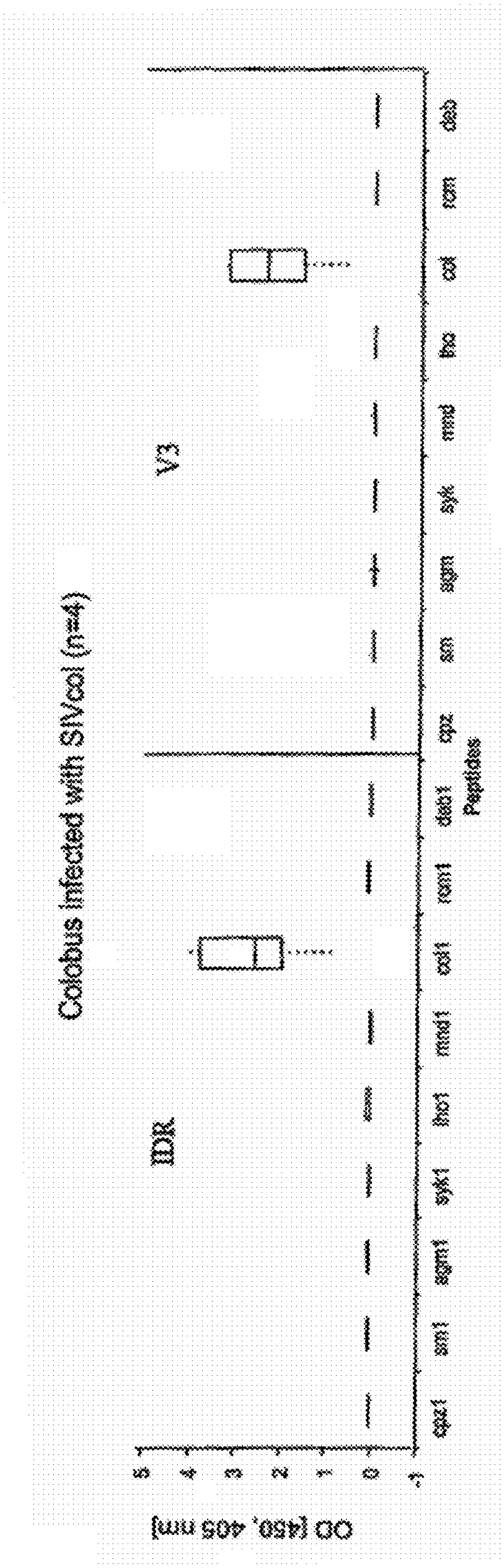
FIG. 3 is a graph showing the optical density (OD) results for an enzyme immunoassay performed on samples from colobus monkeys infected with SIVcol as described herein that utilized both a detection component (identified in FIG. 3 as "IDR") and a differentiation component (identified in FIG. 3 as "V3").

The reactivity of sera from SIVcol infected colobus monkeys was the best in terms of sensitivity and specificity for both IDR and V3 components. All 4 positive specimens reacted solely with SIVcol peptides in both assays as depicted in FIG. 3. This may not be surprising given the high genetic distance of SIVcol from all others lineages. Two SIV positive specimens from red-capped mangabeys infected with SIVrcm were also evaluated, and all were detected by the presently described system in both IDR and V3.

Although the talapoin monkey peptides were not included in the assay (because sequences were not available), 4 specimens were evaluated from infected talapoin monkeys. All were detected in the IDR component of the test by their cross-reactivity to HIV2, AGM, RCM and Sykes MAPs. There was no reactivity with any of the V3 MAPs included in our assay. However, the cross-reactivity in the IDR component demonstrates that previously un-identified SIV strains could be detected by the presently described assays.

The 93 SIV negative specimens from various monkeys did not show any reactivity to their homologous MAPs. The specimens from SFV-infected, but SIV negative, monkeys did not show any reactivity with the 2 gene regions of the assay.

Samples from two SIVmnd-infected mandrills and two SIVdeb-infected DeBrazza'a monkeys were seronegative using a commercially available HIV-1/2 peptide EIA yet were seroreactive to their homologous IDR and V3 MAPs in the assay disclosed herein and were confirmed seropositive using an HIV-2 WB assay.

Table 3 below shows the sensitivities and specificities of the various simian reference groups in terms of reactivities of each specific SIV antibodies against their homologous MAPs. Sensitivities of 100% were obtained for all but two lineages; specificity was 100% for all peptides.

TABLE 3

Sensitivities and specificities from non-human reference panel specimens based on reactivities of each SIV antibodies against their homologous MAPs

| | Positive samples | | | | Negative samples | | | |
|---|---|---|---|---|---|---|---|---|
| panel | nbr. | region | PEIA + | Sensitivity | nbr. | region | PEIA − | specificity |
| SIVsm | 16 | IDR | 16 | 100% | 6+ | IDR | 6+ | 100% |
| | 16 | V3 | 16 | 100% | 6 | V3 | 6 | 100% |
| SIVagm | 9 | IDR | 9 | 100% | 10 | IDR | 10 | 100% |
| | 9 | V3 | 9 | 100% | 10 | V3 | 10 | 100% |
| SIVsyk | 4 | IDR | 4 | 100% | 2 | IDR | 2 | 100% |
| | 4 | V3 | 3 | 75% | 2 | V3 | 2 | 100% |
| SIVcpz | 3 | IDR | 3 | 100% | 3 | IDR | 3 | 100% |
| | 3 | V3 | 2 | 66.60% | 3 | V3 | 3 | 100% |
| SIVl'hoest | 2 | IDR | 2 | 100% | 1 | IDR | 1 | 100% |
| | 2 | V3 | 2 | 100% | 1 | V3 | 1 | 100% |
| SIV col | 4 | IDR | 4 | 100% | 31 | IDR | 31 | 100% |
| | 4 | V3 | 4 | 100% | 31 | V3 | 31 | 100% |

2. Human Reference Panel

There was no significant reactivity observed with the 198 seronegative samples collected in U.S. blood banks.

The 43 HIV-2 specimens reacted specifically with the SIVsm/HIV-2 gp36 MAP as well as the SIVagm MAP. Some cross-reactivities were also found with SIVrcm, SIVsyk and to a lesser extend with SIVlhoest. The V3 component showed reactivities only to SIVsm and SIVagm peptides.

The specimens from HTLV infected individuals did not show any reactivity to the SIV MAPs, except one of the 44 showed some low reactivity with the SIVcol peptide with the IDR peptide; no reactivity with V3. Likewise one of the 18 malaria specimens showed a low reactivity to SIVcpz MAP in IDR while no reactivity was found with the V3. There was no reactivity observed with any of the 4 specimens obtained from persons infected with measles.

With respect to the testing of HIV negative plasma samples from Cameroon, of the samples showing an EIA OD>1 in IDR for an SIV peptide, 17.1% were observed in the HE, 7.8% in LE, and 2.3% in G. One sample collected from our general population reacted to the Colobus peptide in both IDR (OD=1.250) and V3 (OD=1.798).

In summary, the performance of the presently disclosed MAP assay is efficient in detecting and discriminating primate lentiviral infections. SIV infected simian specimens were correctly identified with the IDR assay, even occasionally exhibiting broad cross-reactivity. This cross-reactivity can be a favorable characteristic since it allows one to detect divergent SIV strains for which sequences were unavailable for designing MAPs. The V3 component was more lineage specific in reactivity. Interestingly, the specimen from a person occupationally infected with SIVsm (ref) was detected by the assay, indicating that it will have considerable utility for screening the human population for potential exposures or infections with SIV strains that hold the possibility of infecting our blood supply and seed new emerging infectious diseases. The testing of the HIV negative plasma samples from Cameroon further confirmed that the assay has utility for screening human populations for exposures of infections with SIV strains. The testing of the HIV negative samples from Cameroon showed a strong statistical correlation with exposure to non-human primate blood or body fluids or keeping primates as pets.

A total of 93 sera from various species of uninfected monkeys were also used for evaluation. All were non reactive to all MAPs, thus demonstrating the high specificity of the MAP assay. Also specimens from individuals with a number of endemic infections did not produce any significant reactivity that could compromise the specificity of the assay to SIV only. Concerning HIV positive specimens, cross-reactivity with SIVcol was remarkably very rare (frequency of only 4.7%), followed by SIVrcm (12.7%) and SIVmnd (14.2%). The highest reactivity was found with SIVcpz (90.5%).

The presently disclosed assays proved to be more sensitive than HIV tests and can be used instead of HIV tests for future SIV studies and sentinel surveillance for potential new cross species transmissions of SIV into humans. The IDR component of the assays is highly sensitive and can be used in the primary screening of samples. The V3 component is more specific but less sensitive and can be used if identification to species level is sought. The combination of these 2 components therefore provides a very effective testing strategy that can be used in serosurveillance, especially for detecting divergent SIV strains in monkeys as well as SIV-like infections in humans. This is enhanced by the use of a comprehensive array of peptides covering all genetically characterized primate lentiviruses. The MAP assays offer an open and flexible technology whereby peptides derived from newly identified non-human primate SIV strains can be progressively included into the system. The possibility of using a wide range of peptides increases the probability/potential of detecting previously unidentified divergent lentiviral strains.

Having illustrated and described the disclosed methods and assays with reference to several examples, it should be apparent that these methods and assays may be modified in arrangement and detail.

What is claimed is:

1. An enzyme immunoassay construct for detecting a primate immunodeficiency virus, comprising:

a first substrate to which is bound a plurality of detection multiple antigenic peptides with a same or different amino acid sequence, each detection multiple antigenic peptide comprising a portion of an immunodominant region of a transmembrane envelope protein of a primate immunodeficiency virus, wherein at least one simian immunodeficiency virus is represented in at least one of the detection multiple antigenic peptides; and a second substrate to which is bound a plurality of differentiation multiple antigenic peptides with a same or different amino acid sequence, each differentiation multiple antigenic peptide comprising a portion of a V3-loop of an envelope protein of a primate immunodeficiency virus, wherein at least one simian immunodeficiency virus is represented in at least one of the differentiation multiple antigenic peptides;

wherein the detection multiple antigenic peptides consist of a core matrix and at least two linear antigenic sequences bonded to the core matrix by β-alanine and d-aspartic acid, each linear antigenic sequence is less than 16 amino acid residues and the β-alanine and d-aspartic acid serving as spacer amino acids between each linear antigenic sequence and the core matrix; and wherein the differentiation multiple antigenic peptides consist of a core matrix and at least two linear antigenic sequences bonded to the core matrix by diaminopropionic acid, each linear antigenic sequence is less than 16 amino acid residues and diminopropionic acid serving as a spacer amino acid between each linear antigenic sequence and the core matrix.

2. The immunoassay construct of claim 1, wherein the detection multiple antigenic peptide comprise a portion of the immunodominant region of the transmembrane protein gp41 or gp36, and the differentiation multiple antigenic peptide comprise a portion of the V3-loop of the envelope protein gp120.

3. The immunoassay construct of claim 1, wherein each linear antigenic sequence of the detection multiple antigenic peptide comprise 5 to 15 amino acid residues, and each linear antigenic sequence of the differentiation multiple antigenic peptide comprise 5 to 15 amino acid residues.

4. The immunoassay construct of claim 1, wherein the immunoassay does not include any detection multiple antigenic peptide from a human immunodeficiency virus and any differentiation multiple antigenic peptide from a human immunodeficiency virus.

5. The immunoassay construct of claim 1, wherein one or more of the linear antigenic sequences of the detection multiple antigenic peptide is WGCSGKAVCYT (SEQ ID NO: 1).

6. The immunoassay construct of claim 1, wherein one or more of the linear antigenic sequences of the differentiation multiple antigenic peptide is RGEVQIGPGMTFYNI (SEQ ID NO: 14).

7. The immunoassay construct of claim 1, wherein all of the linear antigenic sequences of the detection multiple antigenic peptides are WGCSGKAVCYT (SEQ ID NO: 1) and the linear antigenic sequence of the differentiation multiple antigenic peptides are RGEVQIGPGMTFYNI (SEQ ID NO: 14).

8. The immunoassay construct of claim 1, wherein one or more of the linear antigenic sequence of the detection multiple antigenic peptide consists of a sequence set forth in (SEQ ID NO: 31)

$X_1GCX_4X_5X_6X_7X_8CX_{10}T$ wherein $X_1$ is W, I or F;

$X_4$ is S, A or Q;

$X_5$ is G, D, F, W or N;

$X_6$ is K, R, M, S, A;

$X_7$ is A, V or Q;

$X_8$ is V, or I; and $X_{10}$ is Y, H or R.

9. The immunoassay construct of claim 1, wherein the detection multiple antigenic peptides and the differentiation multiple antigenic peptides each consist of four linear antigenic sequences bonded to their respective core matrix.

10. The immunoassay construct of claim 1, wherein there are a plurality of detection multiple antigenic peptides and a plurality of differentiation multiple antigenic peptides, and all recognized SIV strain epitopes are represented in at least one of the detection multiple antigenic peptide or the differentiation multiple antigenic peptide.

11. The immunoassay construct of claim 1, wherein one or more of the linear antigenic sequences of the differentiation multiple antigenic peptides is VLPVTIMSGLVFHSQ (SEQ ID NO: 15).

12. The immunoassay construct of claim 1, wherein one or more of the linear antigenic sequences of the differentiation multiple antigenic peptides is VLPVTIMAGLVFHSQ (SEQ ID NO: 16).

13. The immunoassay construct of claim 1, wherein one or more of the linear antigenic sequences of the differentiation multiple antigenic peptides is IKNIQLAAGYFLPVI (SEQ ID NO: 17).

14. The immunoassay construct of claim 1, wherein one or more of the linear antigenic sequences of the differentiation multiple antigenic peptides is EVSTISSTGLLFYYG (SEQ ID NO: 18).

15. The immunoassay construct of claim 1, wherein one or more of the linear antigenic sequences of the differentiation multiple antigenic peptides is HRNLNTANGAKFYYE (SEQ ID NO: 19).

16. The immunoassay construct of claim 1, wherein one or more of the linear antigenic sequences of the differentiation multiple antigenic peptides is VKGISLATGVFISLR (SEQ ID NO: 20).

17. The immunoassay construct of claim 1, wherein one or more of the linear antigenic sequences of the differentiation multiple antigenic peptides is IVSVPSASGLIFYHG (SEQ ID NO: 21).

18. The immunoassay construct of claim 1, wherein one or more of the linear antigenic sequences of the differentiation multiple antigenic peptides is YRAVHMATGLSFYTT (SEQ ID NO: 22).

19. The immunoassay construct of claim 1, wherein one or more of the linear antigenic sequences of the detection multiple antigenic peptide is, IGCANMQICRT (SEQ ID NO: 8), or FGCAWRQVCHT (SEQ ID NO: 9).

20. The immunoassay construct of claim 1, wherein one or more of the linear antigenic sequences of the differentiation multiple antigenic peptides are selected from one or more of one of SEQ ID NOS: 14-22.

21. An enzyme immunoassay construct for detecting a primate immunodeficiency virus, comprising:

a plurality of detection multiple antigenic peptides comprising a portion of an immunodominant region (IDR) of a transmembrane protein of a primate immunodeficiency virus and the plurality of detection multiple antigenic peptides comprising a detection multiple antigenic peptide comprising an SIVcpz IDR, a detection multiple antigenic peptide comprising an SIVsyk IDR and a detection multiple antigenic peptide comprising an SIVdeb IDR; and a plurality of differentiation multiple antigenic peptides comprising a portion of a V3-loop of an envelope protein of a primate immunodeficiency virus and the plurality of differentiation multiple antigenic peptides comprise a differentiation multiple antigenic peptide comprising a portion of a simian immunodeficiency virus (SIV)cpz V3-loop, a differentiation, multiple antigenic peptide comprising a portion of a SIVsyk V3-loop and a differentiation multiple antigenic peptide comprising a portion of a SIVdeb V3-loop, wherein the plurality of detection multiple antigenic peptides and the plurality of differentiation multiple antigenic peptides are immobilized on a single substrate respectively;

wherein each of the detection multiple antigenic peptide consists of a core matrix and at least two linear antigenic sequences bonded to the core matrix by β-alanine and d-aspartic acid, each linear antigenic sequence is less than 16 amino acid residues and the β-alanine and d-aspartic acid serving as spacer amino acids between each linear antigenic sequence and the core matrix;

wherein each of the differentiation multiple antigenic peptide consists of a core matrix and at least two linear antigenic sequences bonded to the core matrix by diaminopropionic acid, each linear antigenic sequence is less than 16 amino acid residues and diminopropionic acid serving as a spacer amino acid between each linear antigenic sequence and the core matrix.

22. The immunoassay construct of claim 21, wherein each linear antigenic sequence of the detection multiple antigenic peptide comprises 5 to 15 amino acid residues, and each linear antigenic sequence of the differentiation multiple antigenic peptide comprises 5 to 15 amino acid residues.

23. The immunoassay construct of claim 21, wherein one or more of the linear antigenic sequences of the detection multiple antigenic peptide comprising the SIVcpz IDR is WGCSGKAVCYT (SEQ ID NO: 1) and the linear antigenic sequences of the differentiation multiple antigenic peptide comprising the SIVcpz V3-loop is RGEVQIGPGMTFYNI (SEQ ID NO: 14).

24. The immunoassay construct of claim 21, wherein each detection multiple antigenic peptide and each differentiation multiple antigenic peptide consists of four linear antigenic sequences bonded to their respective core matrix.

25. An enzyme immunoassay construct for detecting a primate immunodeficiency virus, comprising:

a first substrate to which is bound a plurality of detection multiple antigenic peptides, each detection multiple antigenic peptide comprising a portion of an immunodominant region of a transmembrane envelope protein of a primate immunodeficiency virus, wherein at least one simian immunodeficiency virus is represented in at least one of the detection multiple antigenic peptides; and a second substrate to which is bound a plurality of differentiation multiple antigenic peptides, each differentiation multiple antigenic peptide comprising a portion of a V3-loop of an envelope protein of a primate immunodeficiency virus, wherein at least one simian immunodeficiency virus is represented in at least one of the differentiation multiple antigenic peptides;

wherein the detection multiple antigenic peptides comprise of a core matrix and four linear detection antigenic sequences bonded to the core matrix by β-alanine and d-aspartic acid, each linear detection antigenic sequence is WGCSGKAVCYT (SEQ ID NO: 1) and the β-alanine and d-aspartic acid serve as spacer amino acids between each linear detection antigenic sequence and the core matrix; and wherein the differentiation multiple antigenic peptides comprise of a core matrix and four linear antigenic sequences bonded to the core matrix by diaminopropionic acid, each differentiation linear antigenic sequence is RGEVQIGPGMTFYNI (SEQ ID NO: 14) and diminopropionic acid serves as a spacer amino acid between each differentiation linear antigenic sequence and the core matrix.

* * * * *